US 6,612,999 B2

(12) United States Patent
Brennan et al.

(10) Patent No.: US 6,612,999 B2
(45) Date of Patent: Sep. 2, 2003

(54) BALLOON ACTUATED GUIDE CATHETER

(75) Inventors: Lawrence Brennan, Temecula, CA (US); Neil Becker, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 83 days.

(21) Appl. No.: 10/011,084

(22) Filed: Dec. 6, 2001

(65) Prior Publication Data

US 2003/0109810 A1 Jun. 12, 2003

(51) Int. Cl.[7] .......................... A61B 5/00; A61M 25/00
(52) U.S. Cl. ...................................................... 600/585
(58) Field of Search .......................... 600/585; 604/509, 604/28, 6.14, 530; 606/194, 41, 21

(56) References Cited

U.S. PATENT DOCUMENTS 5,733,248 A * 3/1998 Adams et al. .............. 600/585
5,916,193 A * 6/1999 Stevens et al. ............. 604/509
2002/0087156 A1 * 7/2002 Maguire et al. ............. 606/41
2002/0183730 A1 * 12/2002 Reu et al. .................... 606/21

* cited by examiner

Primary Examiner—Max F. Hindenburg
Assistant Examiner—Brian Szmal
(74) Attorney, Agent, or Firm—Crawford Maunu PLLC

(57) ABSTRACT

A guide catheter employs a flexible shaft having a preformed bend at a distal end. An inflatable member is disposed on the flexible shaft and encompasses at least part of the pre-formed bend. The flexible shaft contains an inflation lumen in fluid connection with the inflatable member. Inflation of the inflatable member causes a deflection of the distal end of the flexible shaft. The guide catheter includes an inflation mechanism in fluid connection with the inflation lumen for pressurizing and depressurizing the inflation member. A guide catheter according to the present invention is useful for various medical procedures, including providing access to heart vessels for cardiac lead implantation, EP mapping, and angiography/venography.

25 Claims, 6 Drawing Sheets

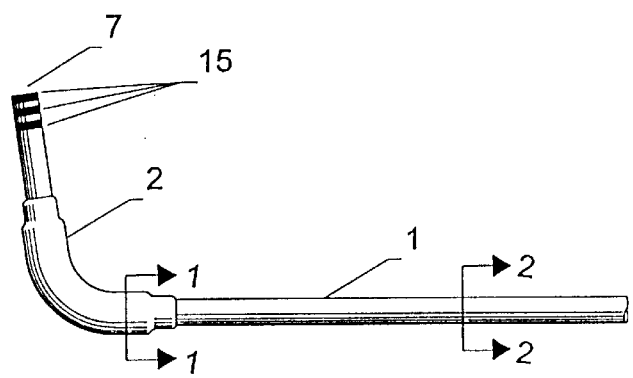
Fig. 2
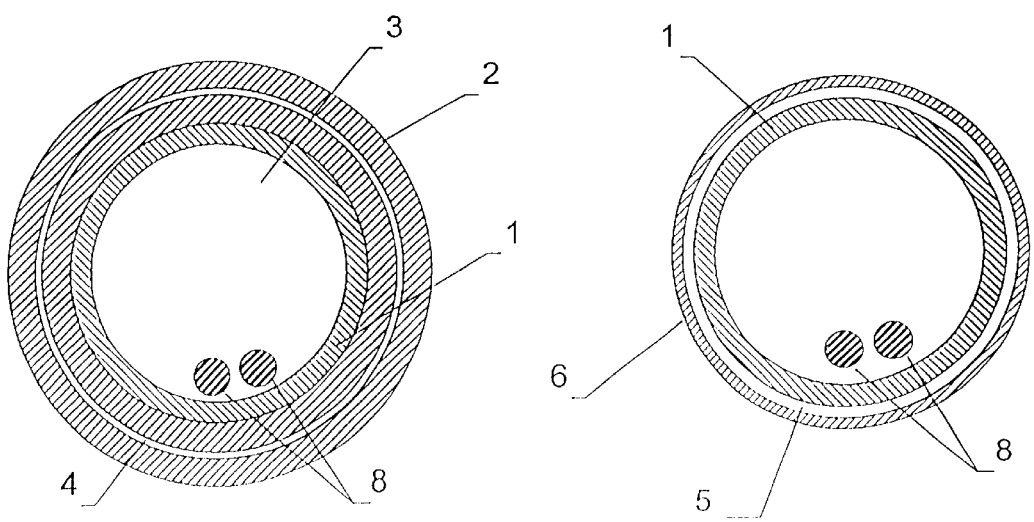
Section 1-1
Fig. 3
Section 2-2
Fig. 4

Section 3-3

Section 4-4

BALLOON ACTUATED GUIDE CATHETER

FIELD OF THE INVENTION

The invention relates generally to guide catheters, and more particularly to guide catheters utilizing a balloon actuated, selectively shapeable distal tip.

BACKGROUND OF THE INVENTION

Guiding catheters are instruments that allow a physician to locate and cannulate vessels in a patient's heart for performing various medical procedures, including venography and implanting of cardiac pacing devices. Cannulating heart vessels requires navigating a small diameter, flexible guide through the convoluted vasculature into a heart chamber, and then into a destination heart vessel. Once the destination heart vessel is reached, the catheter acts as a conduit for insertion of payloads into the vessel.

A commonly accessed destination vessel for cardiac pacing lead insertion is the coronary sinus. A pre-shaped guiding catheter is typically used to blindly locate the coronary sinus ostium. This endeavor, however, is complicated by the fact that the location of the coronary sinus ostium may vary appreciably from one patient to another, especially among patients with diseased hearts. Oftentimes, the clinician is entirely unable to locate the coronary sinus ostium using the guiding catheter, and must resort to finding the ostium by "mapping" (interpreting localized bipolar waveforms) using an electrophysiological (EP) catheter and an ECG monitor. After the ostium is located, the guiding catheter is typically used to inject radiographic contrast media into the coronary sinus to highlight the associated venous system, and then a pacing lead is installed within one of the coronary branches.

Complicating this scenario is the dynamic structural deformation of the heart chambers that occurs from normal cardiac activity during the procedure. This further increases the difficulty of guiding a catheter to its destination. Presently, a considerable amount of time is often spent by the physician when manipulating such catheters within cardiac structures, such as the right atrium, simply trying to locate an anatomical feature of interest, such as the coronary sinus ostium.

Guiding catheter systems are typically configured with a profile that is optimized for the intended method of access. In the case of accessing the coronary sinus via the right atrium, a catheter with a distal contour including a relatively sharp bend will point the catheter towards the likely location of the coronary sinus once the right atrium is reached. The contours of pre-shaped guiding catheters are generally fixed, and this is typically achieved in production by constraining the distal end within a shaping fixture while warming them until they assume the intended shape (i.e., by "heat setting" their polymer shaft).

A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations. Fixed shape catheters may require a time consuming trial and error process of inserting and removing different shapes until the destination vessel is successfully accessed.

Steerable catheters are also used for various guiding applications. Steerable catheters typically rely on an integral steering mechanism which includes a mechanical linkage to a deflection point at the catheter's distal end. These devices can be effective in allowing dynamic reshaping of the catheter's distal end, however they are not ideal for all situations. The linkage usually has some clearance within the lumen to allow for easier longitudinal movement of the linkage. The clearance can result in backlash when the steering mechanism is operated. Depending on the length and deployed shape of the catheter, backlash of a steered catheter may render it difficult to operate.

There is a need for an improved guide catheter for accessing heart vessels that can dynamically account for anatomical variations and defects associated with the destination structures. The present invention fulfills these and other needs, and addresses other deficiencies of prior art implementations and techniques.

SUMMARY OF THE INVENTION

To overcome the limitations in the prior art described above, and to overcome other limitations that will become apparent upon reading and understanding the present specification, the present invention discloses a steerable guide catheter that can provide access to venous structures for medical procedures.

According to one embodiment of the invention, a guide catheter includes a flexible shaft having a pre-shaped distal bend and an inflation lumen. An inflatable member is disposed on an external surface of the flexible shaft in fluid connection with the inflation lumen. The inflatable member encompasses at least part of the pre-shaped distal bend of the flexible shaft. Inflation and deflation of the inflatable member changes a shape of the pre-shaped distal bend. The guide catheter includes an inflation mechanism in fluid connection with a proximal end of the inflation lumen. The inflation mechanism selectably pressurizes and depressurizes the fluid within the inflation lumen to respectively inflate and deflate the inflatable member.

According to another embodiment of the present invention, the guide catheter includes a flexible shaft having a pre-shaped distal bend, an inflation lumen, and an inflatable section disposed along at least part of the pre-shaped distal bend. The inflatable section is in fluid connection with the inflation lumen. The inflatable section changes a shape of the pre-shaped distal bend upon inflation and deflation of the inflatable section. An inflation mechanism is in fluid connection with a proximal end of the inflation lumen. The inflation mechanism selectably pressurizes and depressurizes the fluid within the inflation lumen to respectively inflate and deflate the inflatable section.

In one configuration, the flexible shaft may further include an open lumen. The open lumen can be adapted to receive a payload. The open lumen can also be adapted to receive an injection of a contrast media for mapping blood vessels.

In one arrangement, the inflation lumen is disposed along an external surface of the flexible shaft. In an alternate arrangement, the inflation lumen is disposed within the flexible shaft. In a configuration of a guide catheter according to the present invention, the inflatable member comprises an occlusion balloon.

The inflatable member can be arranged to encompass a partial circumferential angle of a cross section of the flexible shaft. The partial circumferential angle in this arrangement can range from about 90 degrees to about 180 degrees.

In one configuration of a catheter according to the present invention, a distal end of the flexible shaft is steerable by rotation of a proximal end of the flexible shaft. The guide catheter may further include at least one electrode disposed on a distal end of the flexible shaft and at least one electrical conductor disposed along the flexible shaft and coupled to the at least one electrode.

In an embodiment of the present invention, a method of inserting a guide catheter into a patient's blood vessel includes providing a guide catheter. The guide catheter includes a flexible shaft having a pre-shaped distal bend, an inflation lumen, and an inflatable section disposed along at least part of the pre-shaped distal bend. The inflatable section is in fluid connection with the inflation lumen. The inflatable section changes a shape of the pre-shaped distal bend upon inflation and deflation of the inflatable section. An inflation mechanism is in fluid connection with a proximal end of the inflation lumen. The inflation mechanism selectably pressurizes and depressurizes the fluid within the inflation lumen to respectively inflate and deflate the inflatable section.

The method further involves inserting a distal end of the flexible shaft through the patient's venous system via an access vessel. The inflation mechanism is actuated to selectably inflate and deflate the inflatable section. Inflating and deflating the inflation mechanism changes the shape of the pre-shaped distal bend for finding and cannulating the blood vessel.

The method can further involve, after finding and cannulating the blood vessel, distally advancing the flexible shaft to seat the distal end of the flexible shaft in the blood vessel. A payload is then inserted through a proximal end of the flexible shaft for implanting the payload into the blood vessel. The payload may include a pacing lead. In another aspect, the payload may include an occlusion device.

The method can also involve injecting a contrast media into the flexible shaft for mapping of blood vessels after finding and cannulating the blood vessel. In one aspect of the method, the blood vessel is the coronary sinus of the patient's heart and the access vessel is the right atrium accessed via the superior vena cava.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 2 is an external view of a distal end of a catheter embodying features of the present invention;

FIG. 3 is a cross-section of an inflation member corresponding to section 1—1 of FIG. 2;

FIG. 4 is a cross-section of an inflation lumen corresponding to section 2—2 of FIG. 2;

Figure 1:
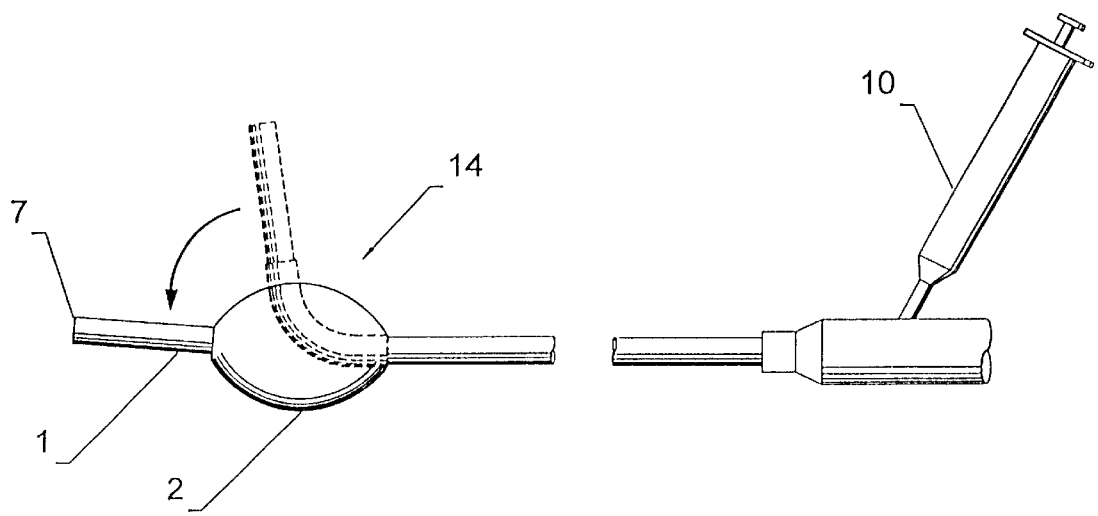
FIG. 1 is an external view of a catheter embodying features of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

With reference to FIG. 1, a guide catheter is shown embodying features of the present invention. The guide catheter includes a flexible shaft 1, an inflatable member 2, and an inflation mechanism 10. The inflation mechanism 10 is typically mounted at a proximal end of the guide catheter and can include a syringe or pump. The use and construction of suitable inflation mechanisms are well known in the art. For example, a prior art inflation mechanism designed for inflating an occlusion balloon with saline solution would function well in this application.

The flexible shaft 1 is configured with dimensions appropriate for the intended venous/arterial access path of a given medical procedure. For example, in a cardiac access application, the flexible shaft 1 may be formed with an outer diameter from about 5 French to about 10 French, and the flexible shaft 1 may have a length of about 40 cm to about 60 cm. The flexible shaft 1 may be fabricated using a polymer tube formed from a material such as urethane, epoxy or Pebax.

An alternate construction of the flexible shaft 1 includes a multi-layer tube design. One particular multi-layer tube design includes an inner lubricious liner, a braid, and an outer jacket. The lubricious liner is typically formed from a material such as PTFE and is disposed within an open lumen of the flexible shaft 1. The braid is typically located between the lubricious liner and outer jacket. The braid can provide longitudinal stiffness to ease advancement of the flexible shaft 1 through blood vessels, as well as helping to prevent kinking of the flexible shaft 1. The braid is usually constructed from a weave of stainless steel wire or ribbon, although a non-metallic fiber braid may also work in this application. The outer jacket is typically a high durometer polymer such as Pebax. The outer jacket provides the flexible tube 1 a smooth and durable outer surface.

The flexible tube 1 has a pre-shaped distal bend 14 that can be thermoset on the flexible tube 1 during manufacture. The profile and dimensions of the pre-shaped distal bend 14 are particular to the intended guiding application. For example, in procedures involving accessing the coronary sinus from the right atrium, a J- or U-shaped distal bend may be appropriate.

The inflatable member 2 is disposed on the flexible shaft 1 and encompasses at least part of the pre-shaped distal bend 14. In this configuration, inflation of the inflatable member 2 can change a shape of the pre-shaped distal bend 14. The inflatable member 2 is shaped to apply forces to the pre-shaped distal bend 14 upon inflation of the inflatable member 2. These forces cause a shape change of the pre-formed distal bend 14 that serves to adjustably steer a distal tip 7 of the flexible shaft 1. The ability to adjustably steer the distal tip 7 of the flexible shaft 1 advantageously allows a guide catheter according to the present invention to account for variability along the venous or arterial pathway. A shape change initiated by the inflatable member 2 is indicated in FIG. 1, with the initial and changed shapes of the flexible shaft 1 and inflatable member 2 drawn in dashed and solid lines, respectively. The bold arrow indicates the steering action induced by the shape change.

It can be appreciated by those skilled in the art that the pre-formed distal bend 14 also allows the distal tip 7 of the flexible shaft 1 to be steered by rotating a proximal end of the flexible shaft 1. The flexible shaft 1 transmits a rotation of the shaft's proximal end to the distal tip 7. Use of a multi-layered flexible tube construction as previously described can provide the flexible shaft 1 with a rotational stiffness that is particularly suited for this type of rotational steering. The ability to rotationally steer the distal tip 7 in combination with the selectable deflection of the pre-formed distal bend 14 using the inflatable member 2 provides a guide catheter according to the present invention with a versatile steerable distal tip 7 useful for locating blood vessels, particularly structures within the heart.

Further details of the flexible shaft 1 and inflatable member 2 are illustrated in FIGS. 2, 3, and 4. A distal end of a catheter embodying features of the present invention is shown in an uninflated state in FIG. 2. FIG. 3 is a cross sectional view of the flexible shaft 1 and the inflatable member 2. In this configuration, the flexible shaft 1 includes an open lumen 3. The open lumen 3 is useful in catheters designed for guiding applications, as payloads such as implantable leads can be advanced through the open lumen 3 after the flexible shaft 1 has cannulated a vessel.

As illustrated in FIG. 3, the inflatable member 2 can be substantially annular in shape and disposed on an external surface of the flexible shaft 1. The inflatable member 2 has an internal cavity 4 into which the inflation fluid is introduced. Pressurizing a fluid within an annular inflatable member 2 can result in an inflated shape similar to that illustrated in solid lines in FIG. 1.

FIG. 4 shows a cross section of the flexible shaft 1 proximal to the inflation member 2. In this example, an inflation lumen 5 is substantially annular in shape, the inflation lumen 5 formed by a clearance between the external surface of the flexible shaft 1 and an exterior jacket 6. Such an arrangement can provide a fluid path that connects the inflatable member 2 with a proximal end of the flexible shaft 1, while still allowing the cross sectional shape of the open lumen 3 to remain substantially smooth.

Figure 5:
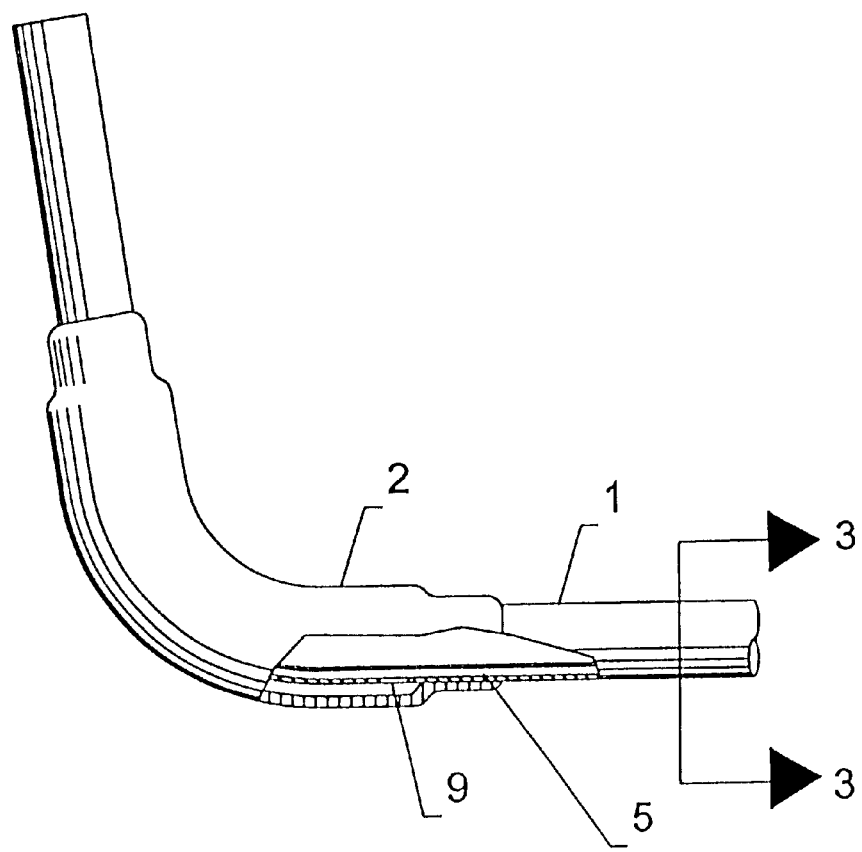
FIG. 5 is a cut-away view of a catheter according to the present invention illustrating a fluid connection between the inflation lumen and the inflation member.
Figure 6:
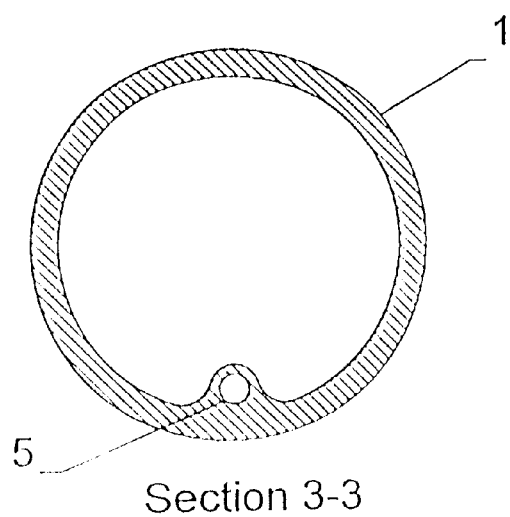
FIG. 6 is a cross-section of a catheter corresponding to section 3—3 of FIG. 5, the cross-section illustrating an alternate inflation lumen configuration.

An alternate arrangement of an inflatable member 2 and an inflation lumen 5 are shown in FIGS. 5 and 6. In FIG. 5, a cut-away is shown at a proximal end of the inflatable member 2. The inflation lumen 5 in this example is formed as an extruded void on a wall of the flexible shaft 1. The arrangement of the inflation lumen 5 within the flexible shaft 1 according to this example is best seen in the cross-sectional view in FIG. 6.

Referring back to FIG. 5, an opening 9 can be provided through an exterior surface of the flexible shaft 1 and into the inflation lumen 5. The opening 9 creates a fluid connection between the inflation lumen 5 and an externally mounted inflatable member 2.

Figure 7:
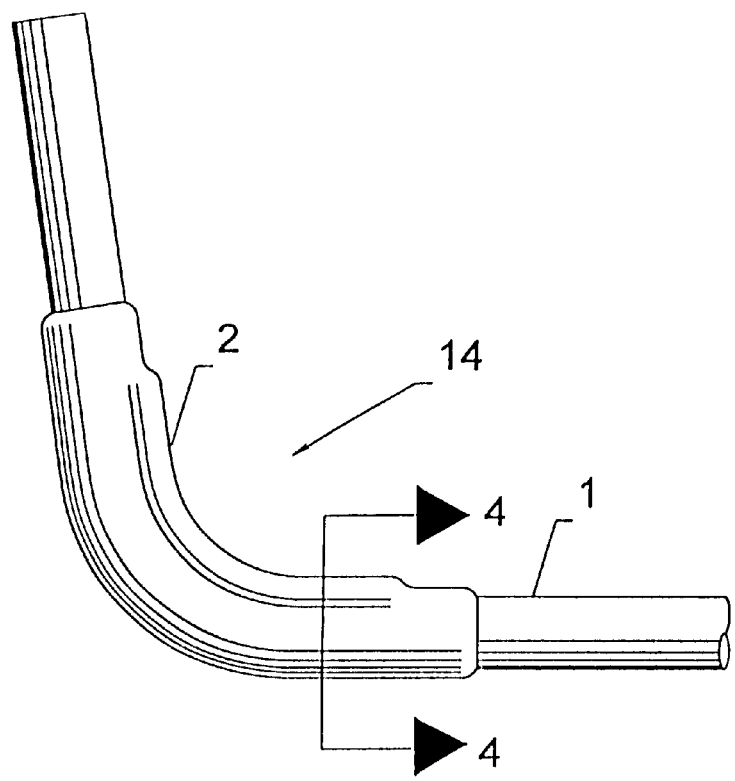
FIG. 7 is an external view of an alternate embodiment of a catheter according to the present invention, the catheter including a partially-annular inflation member.
Figure 8:
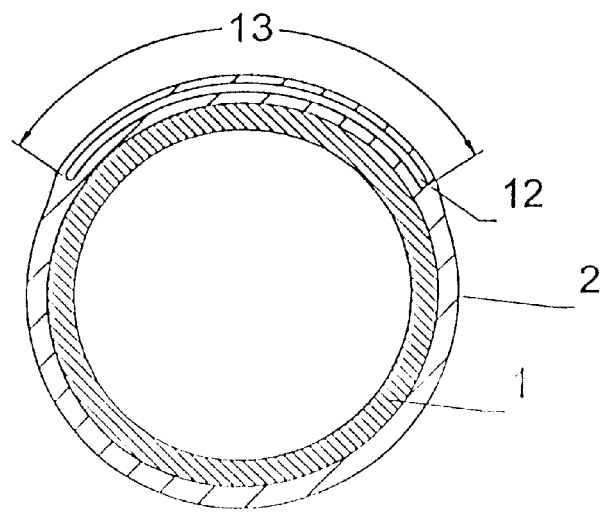
FIG. 8 is a cross sectional view of the inflation member corresponding to section 4—4 of FIG. 7.

An especially useful configuration of an inflatable member 2 is shown in FIG. 7, where a partially-annular inflatable member 2 is illustrated. The inflatable member 2 includes a cavity 12 that extends over a partial perimeter of the flexible shaft. The cavity 12 is best seen in FIG. 8. FIG. 8 is a cross sectional view of the inflatable member 2 and the flexible shaft 1 shown in FIG. 7. The cavity 12 extends over a partial circumferential angle 13 that restricts inflation of the inflatable member 2 to a partially-annular, longitudinally disposed sector of the pre-formed curve 14. An inflation member 2 with various circumferential angles 13 can be manufactured, although an angle 13 ranging from about 90 degrees to about 180 degrees is especially useful in steering the distal tip 7 of the flexible shaft 1.

Figure 9:
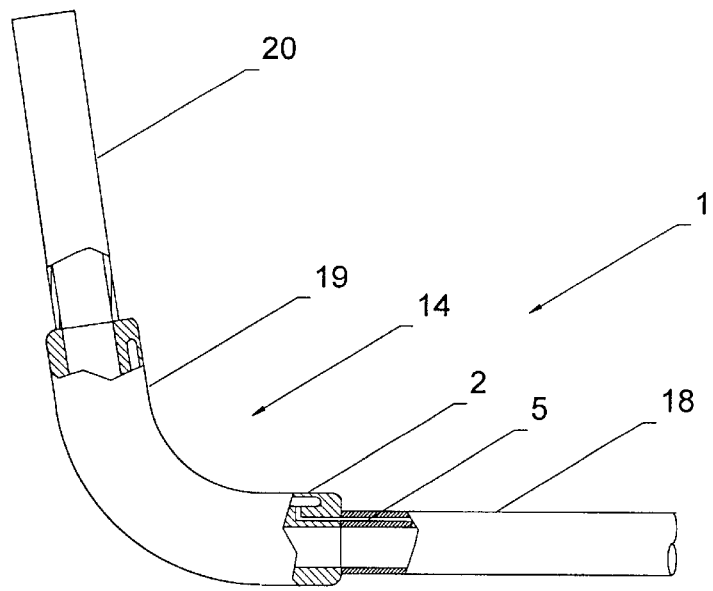
FIG. 9 is a cut-away view of a distal end of a catheter showing an alternate configuration of a flexible shaft and inflatable member.
Figure 10:
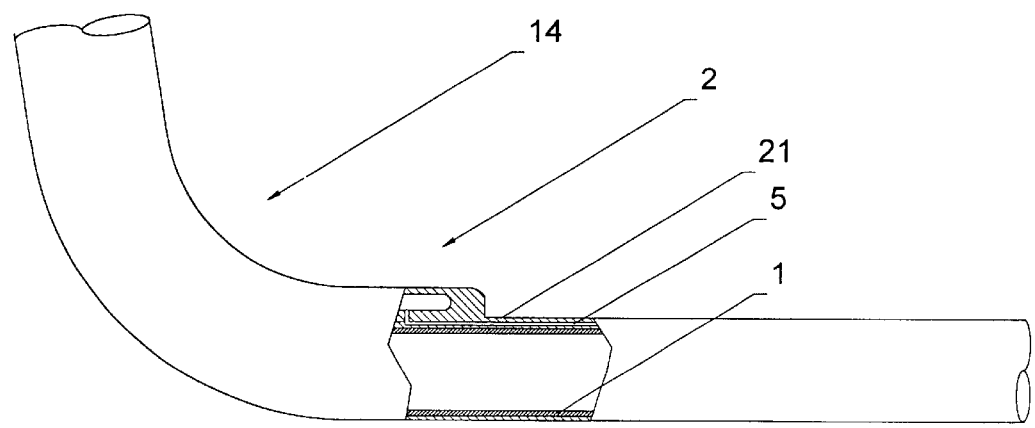
FIG. 10 is a cut-away view of a distal end of a catheter showing another arrangement of a flexible shaft and inflatable member.

The inflatable member 2 in the preceding description was illustrated as an externally mounted balloon. This arrangement is typically produced by forming a balloon of latex or other elastomer to the desired shape and bonding the balloon to a surface of the flexible shaft 1. However, alternate configurations of a flexible shaft 1 with an inflatable member 2 can be produced within the scope of the present invention. For example, as shown in FIG. 8, a shaft could be formed by attaching adjacent longitudinal sections 18, 19, and 20 together. Section 19 contains an integral pre-formed bend 14 and inflatable member 2, while the adjacent proximal section 18 contains an inflation lumen 5. Alternatively, as shown in FIG. 9, a sleeve 21 containing an integral inflation lumen 5 and inflatable member 2 can be bonded over the length of the flexible shaft 1, with the inflatable member 2 encompassing at least part of a pre-formed distal bend 14 on the flexible shaft 1. In such alternate arrangements, introduction of a pressurized fluid into the inflatable member 2 can still provide deflection forces to steer a distal tip 7 of the flexible shaft 1.

It is understood that two or more inflatable members 2 can be provided on a flexible shaft 1 having two or more pre-shaped distal bends 14, each inflatable member 2 encompassing a different pre-shaped distal bend 14. It is also understood that two or more inflatable members 2 can be provided on one pre-shaped distal bend 14 on a flexible shaft, each of the inflatable members 2 encompassing a portion of the flexible shaft's perimeter. Similarly, two or more inflatable members 2 can be adjacently co-located on one pre-formed distal bend 14.

A guide catheter embodying features of the present invention can be adapted for various medical procedures. For example, the flexible shaft 1 can contain an open lumen 3 as seen in FIG. 3. The open lumen 3 can be adapted such that an implantable pacing/defibrillation lead can be passed through the open lumen 3. In such a configuration, the flexible shaft 1 acts as a guide member that cannulates a destination vessel for directing a payload into the destination vessel. In another application, the open lumen 3 can also accept an injection of contrast fluid for purposes of venography or angiography.

Another useful adaptation of a guide catheter according to the present invention includes the mounting of one or more electrodes at a distal end of the flexible shaft 1. This is best seen in FIG. 2, where the electrodes 15 are shown flush mounted to the flexible shaft 1. The electrodes 15 can be used for electrophysiological (EP) purposes, such as EP mapping of structures within the heart. EP electrodes are often fabricated from stainless steel, although the electrodes 15 could be made of platinum, silver or other electrode materials known in the art. A guide catheter according to the present invention can also be adapted to include ablation electrodes. Ablation electrodes are typically formed of platinum/iridium, and can also be mounted as illustrated in FIG. 2. Conductors 8 are coupled to the electrodes 15 and disposed along the flexible guide 1. FIG. 3 shows conductors 8 that are located within the open lumen 3.

A guide catheter according to the present invention can also be employed to occlude blood flow. Occlusion of blood flow is sometimes used in medical procedures such as venography/angiography, wherein occlusion is required during contrast media injection. In one configuration, occlusion can be accomplished by using the inflatable member 2 as an occlusion device. Alternatively, a separate occlusion balloon can be mounted on a distal end of the flexible shaft 1. In an arrangement utilizing a separate occlusion balloon, the flexible shaft can include a second inflation lumen, similar to the inflation lumen 5 shown in FIG. 6.

Figure 11:
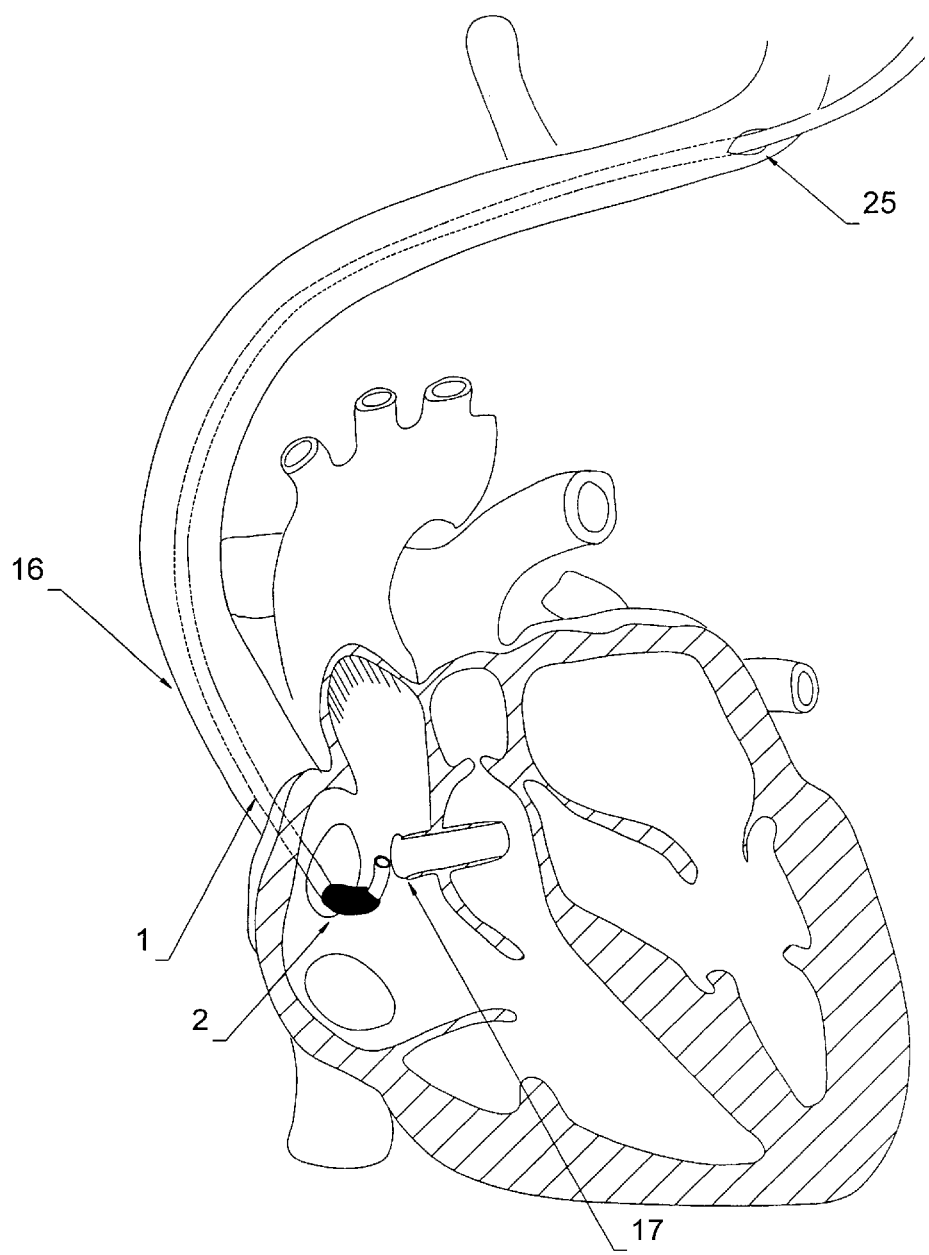
FIG. 11 is a cross sectional view of a heart showing a guide catheter according to the present invention deployed for a coronary sinus cannulation procedure in the right atrium.

Various medical procedures can benefit from the advantages realizable by implementing a guide catheter according to the present invention. For example, guide catheters can provide percutaneous access to various anatomical features, thereby avoiding risky surgery. Common guide catheter applications include providing access to the heart through the vasculature for procedures such as EP mapping, venography/angiography, and implantation of payloads such as pacing leads. To illustrate one guide catheter application, a cardiac pacing lead implantation procedure is described hereinbelow. Particular aspects of this procedure are illustrated in FIG. 11.

Cardiac access procedures usually begin by creating a percutaneous opening 25 into an access vessel. Common access vessels used for cardiac implantation include the left cephalic vein and the left subclavian vein. The distal end of the flexible shaft 1 can be introduced by a clinician into the percutaneous opening 25, after which the flexible shaft 1 is distally advanced through the access vessel and into the heart. When a distal end of the flexible shaft 1 has entered a chamber of the heart, the clinician attempts to cannulate a destination vessel with the flexible shaft 1.

The destination vessel for cardiac pacing lead implantation is often the coronary sinus 17. In this example, the subclavian or cephalic access will lead the distal end of the flexible shaft 1 to the superior vena cava and into the right atrium of the heart. An opening of the coronary sinus 17 (e.g. the coronary sinus ostium) is accessible from the right atrium. Once the flexible shaft 1 has reached the right atrium, inflating the inflatable member 2 beneficially allows the clinician to probe for the coronary sinus ostium. Further, the clinician can rotate a proximal end of the flexible shaft 1 to further assist in locating the ostium. Once the distal tip 7 of the flexible shaft 1 has located the ostium, the flexible shaft 1 can be distally advanced to cannulate the coronary sinus 17.

After the flexible shaft 1 has cannulated the coronary sinus 17, a radio-opaque contrast media may be injected to map branches of the coronary sinus 17. The blood flow can be occluded before injecting the contrast media by inflating the inflation member 2. Alternatively, a separately attached occlusion balloon can be inflated for this purpose, if the guide catheter is so equipped. Mapping the blood vessels helps identify branch vessels that are candidates for pacing lead implantation.

A pacing lead can be implanted by introducing the pacing lead through the open lumen 3 of the flexible shaft 1. The pacing lead is distally advanced past the distal tip 7 of the flexible shaft 1 and seated into a branch of the coronary sinus 17. Once the pacing lead has been successfully implanted, the flexible shaft 1 can be removed from the heart and vasculature.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guide catheter, comprising:
    a flexible shaft comprising a pre-shaped distal bend and an inflation lumen;
    an inflatable member disposed on an external surface of the flexible shaft in fluid connection with the inflation lumen, the inflatable member encompassing at least part of the pre-shaped distal bend of the flexible shaft, inflation and deflation of the inflatable member changing a shape of the pre-shaped distal bend; and
    an inflation mechanism in fluid connection with a proximal end of the inflation lumen, the inflation mechanism selectably pressurizing and depressurizing the fluid within the inflation lumen to respectively inflate and deflate the inflatable member.

2. A guide catheter according to claim 1, wherein the flexible shaft further comprises an open lumen.

3. A guide catheter according to claim 2, wherein the open lumen is adapted to receive a payload.

4. A guide catheter according to claim 2, wherein the open lumen is adapted to receive an injection of a contrast media for mapping blood vessels.

5. A guide catheter according to claim 1, wherein the inflation lumen is disposed along an external surface of the flexible shaft.

6. A guide catheter according to claim 1, wherein the inflation lumen is disposed within the flexible shaft.

7. A guide catheter according to claim 1, wherein the inflatable member comprises an occlusion balloon.

8. A guide catheter according to claim 1, wherein the inflatable member encompasses a partial circumferential angle of a cross section of the flexible shaft, the partial circumferential angle ranging from about 90 degrees to about 180 degrees.

9. A guide catheter according to claim 1, wherein a distal end of the flexible shaft is steerable by rotation of a proximal end of the flexible shaft.

10. A guide catheter according to claim 1, further comprising:
    at least one electrode disposed on a distal end of the flexible shaft; and
    at least one electrical conductor disposed along the flexible shaft and coupled to the at least one electrode.

11. A guide catheter, comprising:
    a flexible shaft comprising a pre-shaped distal bend, an inflation lumen, and an inflatable section in fluid connection with the inflation lumen, the inflatable section disposed along at least part of the pre-shaped distal bend and changing a shape of the pre-shaped distal bend upon inflation and deflation of the inflatable section; and an inflation mechanism in fluid connection with a proximal end of the inflation lumen, the inflation mechanism selectably pressurizing and depressurizing the fluid within the inflation lumen to respectively inflate and deflate the inflatable section.

12. A guide catheter according to claim 11, wherein the flexible shaft further comprises an open lumen.

13. A guide catheter according to claim 12, wherein the open lumen is adapted to receive a payload.

14. A guide catheter according to claim 12, wherein the open lumen is adapted to receive an injection of a contrast media for mapping blood vessels.

15. A guide catheter according to claim 11, wherein the inflation lumen is disposed along an external surface of the flexible shaft.

16. A guide catheter according to claim 11, wherein the inflation lumen is disposed within the flexible shaft.

17. A guide catheter according to claim 11, wherein a distal end of the flexible shaft is steerable by rotation of a proximal end of the flexible shaft.

18. A guide catheter according to claim 11, further comprising:

at least one electrode disposed on a distal end of the flexible shaft; and at least one electrical conductor disposed along the flexible shaft and coupled to the at least one electrode.

19. A guide catheter according to claim 11, wherein the inflatable section encompasses a partial circumferential angle of a cross section of the flexible shaft, the partial circumferential angle ranging from about 90 degrees to about 180 degrees.

20. A method of inserting a guide catheter into a patient's blood vessel, comprising:

providing a guide catheter comprising:

a flexible shaft comprising a pre-shaped distal bend, an inflation lumen, and an inflatable section disposed along at least part of the pre-shaped distal bend, the inflatable section changing a shape of the pre-shaped distal bend upon inflation and deflation of the inflatable section; and a flexible shaft comprising a pre-shaped distal bend, an inflation lumen, and an inflatable section in fluid connection with the inflation lumen, the inflatable section disposed along at least part of the pre-shaped distal bend and changing a shape of the pre-shaped distal bend upon inflation and deflation of the inflatable section;

inserting a distal end of the flexible shaft through the patient's venous system via an access vessel; and actuating the inflation mechanism to selectably inflate and deflate the inflatable section to change the shape of the pre-shaped distal bend for finding and cannulating the blood vessel.

21. A method according to claim 20, further comprising, after finding and cannulating the blood vessel:

distally advancing the flexible shaft to seat the distal end of the flexible shaft in the blood vessel; and inserting a payload through a proximal end of the flexible shaft for implanting the payload into the blood vessel.

22. A method according to claim 21, wherein the payload comprises a pacing lead.

23. A method according to claim 21, wherein the payload comprises an occlusion device.

24. A method according to claim 20, further comprising injecting a contrast media into the flexible shaft for mapping of blood vessels after finding and cannulating the blood vessel.

25. A method according to claim 20, wherein the blood vessel is the coronary sinus of the patient's heart and the access vessel is the right atrium via the superior vena cava.

* * * * *